United States Patent [19]

DeLuca et al.

[11] 4,201,881
[45] May 6, 1980

[54] 24,24-DIFLUORO-1α,25-DIHYDROXY-CHOLECALCIFEROL

[75] Inventors: Hector F. DeLuca; Heinrich K. Schnoes, both of Madison, Wis.; Nobuo Ikekawa, Tokyo, Japan; Yoko Tanaka, Madison, Wis.; Yoshiro Kobayashi, Tokyo, Japan

[73] Assignee: Wisconsin Alumni Research Foundation, Madison, Wis.

[21] Appl. No.: 24,848

[22] Filed: Mar. 28, 1979

[51] Int. Cl.$^2$ ............................................. C07C 35/32
[52] U.S. Cl. .................................. 568/819; 568/665; 424/343
[58] Field of Search ...................................... 568/819

[56] References Cited
FOREIGN PATENT DOCUMENTS 2259661 6/1973 Fed. Rep. of Germany ........... 568/819

Primary Examiner—Bernard Helfin
Attorney, Agent, or Firm—Howard W. Bremer

[57] ABSTRACT

The invention provides new derivatives of vitamin D, 24,24-difluoro-1α,25-dihydroxycholecalciferol and 24,24-difluoro-1α,25-dihydroxy-5,6-trans-cholecalciferol and processes for preparing the same.

The compounds are characterized by vitamin D-like activity essentially equivalent to the vitamin D-like activity of 1α,25-dihydrocholecalciferol which is considered to be the hormonal form and most active derivative of vitamin D. The compounds of this invention are characterized by their ability to increase intestinal calcium transport, increase serum calcium and to prevent the development of rickets. These compounds would find ready application as a substitute for vitamin D and in the treatment of disease states evincing metabolic calcium and phosphorus deficiencies.

4 Claims, No Drawings

24,24-DIFLUORO-1α,25-DIHYDROXYCHOLECALCIFEROL

The invention described herein was made in the course of work under a grant or award from the Department of Health, Education, and Welfare.

DESCRIPTION

The Government also has rights in this invention pursuant to U.S. Japan Cooperative Grant INT-76-05793 and IPA No. 0001 awarded by the National Science Foundation.

Technical Field

This invention relates to a compound which is characterized by vitamin D-like activity.

More specifically this invention relates to a derivative of vitamin $D_3$.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective, vitamin $D_3$ must be converted in vivo to its hydroxylated forms. For example, the vitamin is first hydroxylated in the liver to form 25-hydroxy-vitamin $D_3$ and is further hydroxylated in the kidney to produce 1α,25-dihydroxy vitamin $D_3$ or 24,25-dihydroxy vitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

Background Art

Since the discovery of biologically active metabolites of vitamin D there has been much interest in the preparation of structural analogs of these metabolites, because such compounds may represent useful therapeutic agents for the treatment of diseases resulting from calcium metabolism disorders. A variety of vitamin D-like compounds have been synthesized. See, for example, U.S. Pat. Nos. 3,741,996 directed to 1α-hydroxycholecalciferol; 3,907,843 directed to 1α-hydroxyergocalciferol; 3,786,062 directed to 22-dehydro-25-hydroxycholecalciferol; 3,906,014 directed to 3-deoxy-1α-hydroxycholecalciferol; and 4,069,321 directed to the preparation of various side chain-fluorinated vitamin $D_3$ derivatives and side chain-fluorinated dihydrotachysterol analogs. Many of these compounds have indeed been shown to possess potent vitamin D-like activity, and some offer other practical advantages, such as relative ease of preparation, or partial selectivity of action, but none has yet been found that is as active in vivo as 1α,25,dihydroxycholecalciferol (1α,25-dihydroxyvitamin $D_3$), now generally considered the target-tissue-active hormonal form of vitamin D.

Disclosure of Invention

A new derivative of vitamin D has now been prepared, which is at least as potent as 1α,25-dihydroxyvitamin $D_3$, as measured by its ability to stimulate calcium transport in intestine or its ability to mobilize calcium from bone. This derivative has been identified as 24,24-difluoro-1α,25-dihydroxycholecalciferol (24,24-difluoro-1α,25-dihydroxyvitamin $D_3$ or 24—$F_2$—1,25(OH)$_2$ $D_3$).

This new derivative may represent a preferred agent for many therapeutic applications, because it is blocked to further metabolism at the carbon 24. It is well known that 1α,25-dihydroxyvitamin $D_3$, can undergo further metabolism in vivo to yield 1α,24R,25-trihydroxyvitamin $D_3$. This 24-hydroxylated form is however less active than 1α,25-dihydroxyvitamin $D_3$ itself, and 24-hydroxylation may indeed represent the first step towards degradation and elimination of this compound from the animal system. In the derivative of the present invention the presence of two fluorine atoms at carbon-24 will, of course, prevent hydroxylation of this carbon atom and the compound is not, therefore, subject to the activity-attenuating metabolism affecting 1,25-dihydroxycholecalciferol. Prevention of this side chain metabolism should permit the maintenance of higher tissue levels of the analog for a longer period of time, a factor of obvious advantage in many therapeutic applications.

BEST MODE FOR CARRYING OUT THE INVENTION 24,24-difluoro-1α,25-dihydroxyvitamin $D_3$ is readily prepared from 24,24-difluoro-25-hydroxyvitamin $D_3$ by in vitro enzymatic hydroxylation of the latter compound at carbon 1 as illustrated in the following schematic:

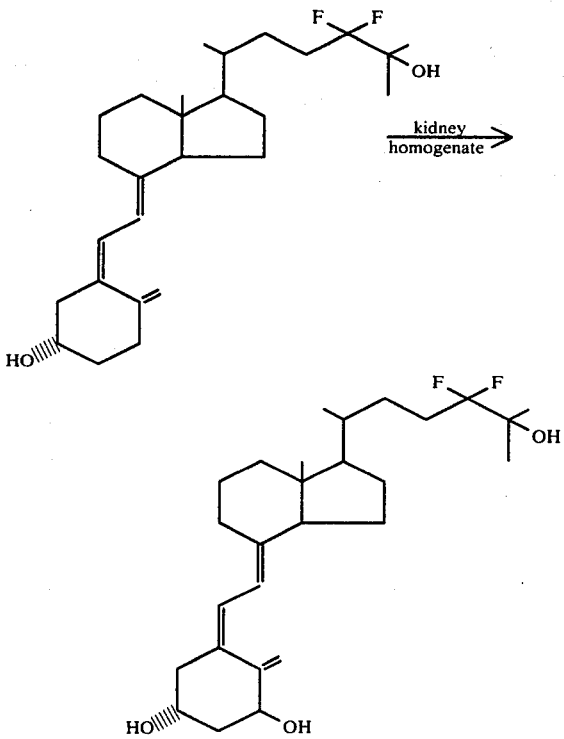

Hydroxylation at carbon 1 is accomplished by incubating the precursor 24,24-difluoro-25-hydroxyvitamin $D_3$ with a homogenate prepared from kidney tissue of vitamin D-deficient chickens. One day-old leghorn chickens are fed a vitamin D-deficient diet containing 1% calcium for one month (Omdahl et al, Biochemistry, 10, 2935–2940 (1971)). They are then killed, their kidneys are removed, and a 20% (w/v) homogenate is prepared in ice-cold 0.19 M sucrose solution containing 15 mM Tris-acetate (trihydroxymethylaminoethane acetate) (pH 7.4) and 1.9 mM magnesium acetate. (Omdahl, J., et al, Biochemistry 10, 2935–2940 (1971)) and (Tanaka, Y., et al, Arch. Biochem. Biophys. 171, 521–526 (1975)).

A typical small-scale incubation involves the addition of 3 μg of 24,24-difluoro-25-hydroxyvitamin D$_3$ (in 25 μl of 95% ethanol) to an aliquot of the kidney homogenate (prepared as described avove and representing about 600 mg of kidney tissue) suspended in 4.5 ml of buffer solution (pH 7.4) which contains 0.19 M sucrose, 1.5 mM Tris-acetate, 1.9 mM magnesium acetate and 25 mM succinate. After shaking the mixture at 37° C. for 2 hours, the reaction is stopped by adding a 2:1 mixture of methanol:CHCl$_3$ solvent. The organic phase of the resulting mixture is separated (gravity settling) and evaporated and the residue containing the desired 24,24-difluoro-1α,25-dihydroxyvitamin D$_3$ is then subjected to chromatographic purification.

The residue, dissolved in 1 ml of CHCl$_3$:hexane (65:35) is applied to Sephadex LH-20 (a hydroxypropyl ether derivative of a polydextran, Pharmacia Corp., Piscataway, N.J.) column (0.7 × 14 cm) packed and equilibrated in CHCl$_3$:hexane (65:35). After elution of 11 ml of solvent (which is discarded) the next 25 ml are collected, evaporated in vacuo, and the residue, dissolved in 1 ml of hexane:CHCl$_3$:MeOH (9:1:1) is chromatographed on Sephadex LH-20 (0.7 × 14 cm) column equilibrated and eluted with hexane: CHCl$_3$:MeOH mixture (9:1:1). The first 9 ml of eluent are discarded and the next 30 ml are collected and the solvent evaporated.

The product is further purified by high pressure liquid chromatography using a model ALC/GPC 204 high pressure liquid chromatograph (Waters Associates, Medford, Mass.) equipped with an ultraviolet detector operating at 254 nm. The sample obtained as above is injected onto a silica gel column (Zorbax-SIL, 0.46 × 25 cm, manufactured by Dupont, Inc.) operating under a pressure of 1000 psi which produces a flow rate of 2 ml/min. Using a solvent system containing 9% of 2-propanol in hexane, the sample is recycled twice through this column (by switching the instrument to its recycle mode) and then collected. Solvent is evaporated and the residue is further purified on a reversed-phase column [Zorbax-ODS (octadecylsilane bonded to a fine grained silica gel) 0.45 × 25 cm, a product of Dupont and Co.] using the same high pressure liquid chromatograph operating at a pressure of 3000 psi. The product is eluted with a solvent mixture of H$_2$O/MeOH (1:3), recycled once and then collected. The collected fractions are evaporated and the residue is rechromatographed on the straight-phase silica gel column (Zorbax-SIL, 0.46 × 25 cm) using conditions exactly as described above. After recycling twice, the sample is collected, and after evaporation of the solvent, pure product is obtained.

The identity of the product as 24,24-difluoro-1α,25-dihydroxyvitamin D$_3$ can be confirmed by its spectroscopic properties. The product shows the typical vitamin D-like ultraviolet absorption with a maximum at 264 nm. The mass spectrum of the product contains a molecular ion at m/e 452 as required for a 24,24-difluoro-derivative of 1α,25-dihydroxyvitamin D$_3$. Fragment ions at m/e 434 and 416 represent elimination of one and two molecules of H$_2$O. Loss of the entire steroid side chain results in the fragment of m/e 287 which, by elimination of one and two molecules of H$_2$O, gives rise to the peaks at m/e 269 and 251. In addition, the spectrum shows prominent peaks at m/e 152 and m/e 134 (152-H$_2$O) which represent ring A fragments and are diagnostic for 1α,3β-dihydroxyvitamin D$_3$ compounds.

The starting material, 24,24-difluoro-25-hydroxyvitamin D$_3$, required for preparation of the 1α-hydroxy analog of this invention can be prepared according to the following process and schematic.

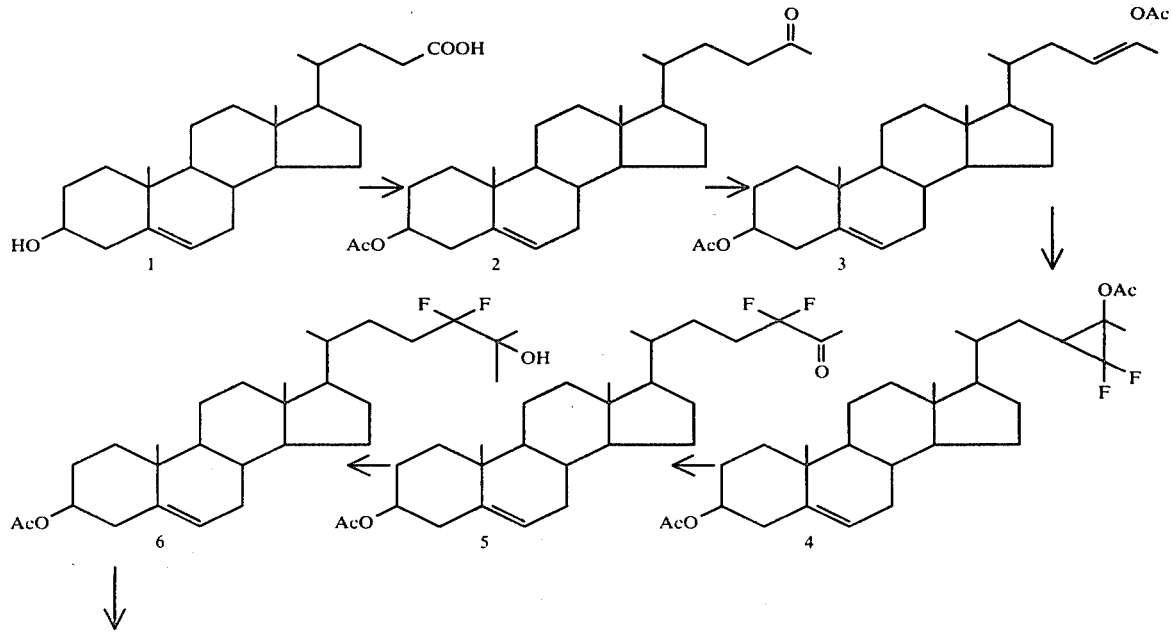

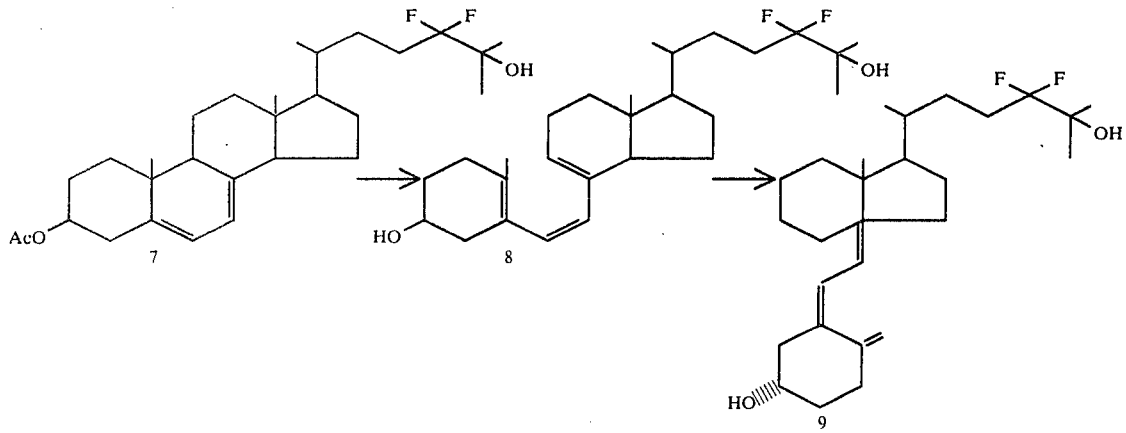

Cholenic acid 1 is treated with dihydropyran in a suitable organic solvent ($CH_2Cl_2$) at 0° in the presence of p-tolene sulfonic acid (PtsOH) and then with 1N NaOH in ethanol at 20° to form the cholenic acid tetrahydropyranyl ether (protection of the hydroxyl group in the A ring). This compound is then treated with an excess of $CH_3Li$ in tetrahydrofuran (THF)-ethyl ether at 0° C. for four hours after which the protective tetrahydropyranyl group is removed by treatment with p-TsOH in $CH_2Cl_2$-methanol for 24 hours at 20° C. Subsequent acetylation ($Ac_2O$-pyridine-$CH_2Cl_2$, 20°, 24 hours) yields the methylketone 2 (mp 148°-151°).

The methylketone 2, when refluxed for seven hours in acetic anhydride in the presence of p-TsOH (enolacetylation) yields the diacetate 3 (mp 109°-110°) (m/e 396 (M-60)). The diacetate is then converted to the difluorocyclopropane 4 by heating with sodium chlorodifluoro-acetate in diglyme at 170° for 0.5 hours (yield, 34%; mp 112°-115°).

Treatment of 4 with LiOH in THF-methanol-water at 20° C. for two hours followed by acetylation ($AC_2O$-pyridine-$CH_2Cl_2$, 20°, 24 hr.) gives, after chromatography on silica gel, the difluoroketone 5, mp 135°-136.5°. (The difluoroketone is obtained in a mixture with the 23(E)- and the 23(Z)- conjugated ketone, with the difluoroketone being separated by chromatography on silica gel.)

The difluoroketone 5 is then reacted with an excess of $CH_3MgI$ in ethyl ether at 0° C. for 15 minutes and is subsequently acetylated ($AC_2O$-pyridine-$CH_2Cl_2$, 20°, 20 hr.) to furnish the 25-carbinol, 6, in 85% yield (mp 163°-164.5°, δ1.28 (6H,s,C—26.27), m/e 420 (M-60)). The carbinol, 6, is allylically brominated by reacting it with N-bromo-succinimide in refluxing $CCl_4$ for 25 minutes. The brominated compound is then directly dehydrobrominated by treatment with s-collidine in refluxing xylene for 15 minutes to give a mixture of the 4,6-diene and the 5,7-diene, 7. The 5,7-diene (λmax 263, 272, 282 and 292 nm) is isolated after treatment of the reaction mixture with p-TsOH in acetone at 20° for 15 hours followed by preparative thin-layer chromatography (benzene-ethyl acetate (15:1), 3 times). The recovered 5,7-diene, after saponification by treatment with 5% KOH-methanol at 20° C. for 15 hours, is irradiated (Hanovia high pressure quartz mercury vapor lamp, model 654A36;200 W) in a mixture of ethanol and benzene for 2.5 minutes at 0° C. to give the previtamin 8 in solution. The irradiated solution is refluxed for one hour and then fractionated by thin-layer chromatography (silica gel, benzene-ethyl acetate, (5:1), 3 times) and high pressure liquid chromatography (Zorbax SIL, 25 cm×2.1 mm i.d., available through the Dupont Co., Wilmington, Delaware) using $CH_2Cl_2$ as eluting solvent to yield 24,24-difluoro-25-hydroxyvitamin $D_3$, 9, (λmax 264 nm, λmin 228 nm, m/e 436 (M+), 421, 418, 403, 377, 271, 253, 136, 118).

Preparation of 24,24-difluoro-1α,25-dihydroxyvitamin $D_3$ can, of course, also be accomplished by purely chemical methods. With 24,24-difluoro-25-hydroxyvitamin $D_3$ as starting material a particularly convenient process involves the direct C-1-hydroxylation via 3,5-cyclovitamin D-intermediates according to the general procedures described by Paaren et al. (Proc. Nat. Acad. Sci., U.S.A. 75, 2080-2081 (1978)). The synthesis is shown in the process schematic below.

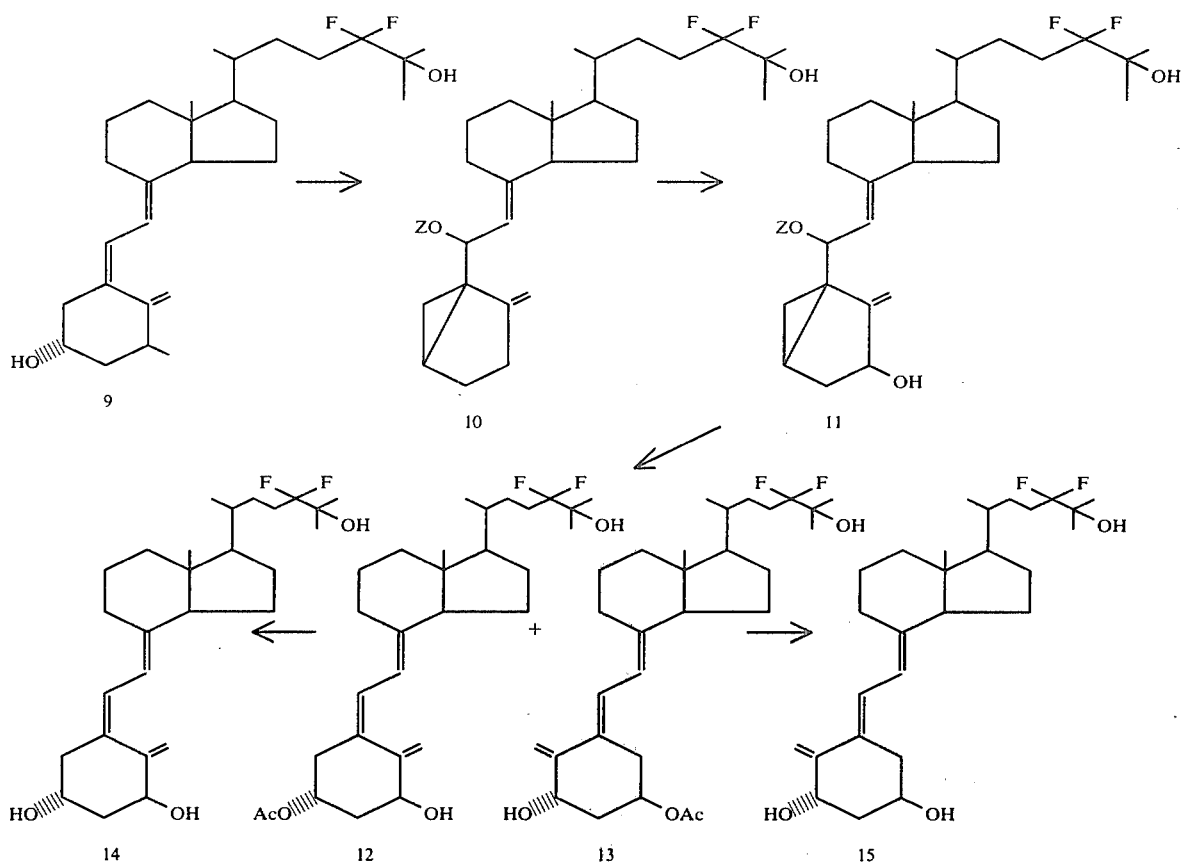

Thus, treatment of a pyridine solution of 24,24-difluoro-25-hydroxyvitamin D$_3$ (9) with 1–1.5 equivalents of p-toluene solfonyl chloride for 24 hours at 3° C. gives, after addition of a saturated solution of NaHCO$_3$, extraction with ether, and subsequent evaporation of ether solvent, the corresponding 3-mono-tosylated derivative. This material is dissolved in anhydrous methanol and then treated with 5–10 equivalents of NaOAc. After warming to 55° C. for 20 hours, the mixture is cooled, diluted with H$_2$O and extracted with ether. The desired product, 24,24-difluoro-25-hydroxy-6-methyl-3,5-cyclovitamin D$_3$ 10, (Z=methyl)following evaporation of the ether solvent, is obtained in 50% overall yield. The use of alternative alcoholic solvents, e.g. ethanol, propanol, etc. in the above reaction yields analogous cyclovitamin D compounds of general structure 10, where Z=ethyl, propyl etc. These analogs are equally useful for the subsequent synthetic steps as described below. If desired, the cyclovitamin D product can be purified by silica gel thin-layer chromatography using hexane/ethyl acetate (8:2) as solvent system, but it can also be used directly for the next step, which involves treatment of the cyclovitamin intermediate, dissolved in a halo-carbon solvent (e.g. CH$_2$Cl$_2$), with SeO$_2$ (0.5 equiv.) and t-butyl hydroperoxide (2 equiv.) according to the conditions described by Paaren et al (supra). After a 15 minute reaction time at room temperature, a 10% NaOH-solution is added, and the product is extracted with ether. The ether phase is washed with aqueous alkali and then with water, evaporated, and after thin-layer chromatography of the residue (using silica gel and hexane/ethylacetate 6:4, as solvent) pure 24,24-difluoro-1α,25-dihydroxy-6-methoxy-3,5-cyclovitamin D$_3$ is obtained (11, Z=Mc) (55% yield). Treatment of this product with glacial acetic acid at 60° for 15 minutes, followed by neutralization of the acetic acid with aqueous alkali and extraction with ether gives, after evaporation of the solvent, a mixture of 24,24-difluoro-1α,25-dihydroxyvitamin D$_3$ 3-acetate (12) and the corresponding 5,6-trans isomer (13) (ratio ca. 3:1). These compounds are conveniently separated by either column chromatography or thin-layer chromatography (e.g. silica gel, hexane:ethylacetate solvent), or high pressure liquid chromatography and the pure 24,24-difluoro-1α,25-dihydroxyvitamin D$_3$ 3-acetate thus obtained is saponified by treatment with base (e.g. 5% NaOH/MeOH, 2 hours, room temperature) to give after extraction with ether and evaporation of ether solvent, the desired analog, 24,24-difluoro-1α,25-dihydroxyvitamin D$_3$ (14) in pure form, exhibiting spectral properties as described for the product generated by enzymatic reaction.

The 5,6-trans-24,24-difluoro-1α,25-dihydroxyvitamin D$_3$ 3-acetate (13) isomer, obtained in pure form after the chromatography step described above, is hydrolyzed in dilute base (5% NaOH/MeOH, 2 hours, room temperature) to yield after ether extraction and evaporation of solvent pure 5,6-trans-24,24-difluoro-1α,25-dihydroxyvitamin D$_3$ (15). This compound shows a mass spectrum very similar to that of the corresponding 5,6-cis-isomer, but exhibits an ultraviolet spectrum with a maximum at 270 nm, characteristic for the 5,6-trans-vitamin D chromophore.

The 5,6-trans-24,24-difluoro-1α,25-dihydroxyvitamin D₃ compound can of course be converted to 24,24-difluoro-1α,25-dihydroxyvitamin D₃ by the well-known photochemical isomerization of the 5,6-double bond, using the method described, for example by Inhoffen et al (Chem. Ber. 90 2544 (1957). Alternatively, the 5,6-trans-3-acetate intermediate (13) obtained from the solvoysis of the cyclovitamin compound as described above, can be isomerized by irradiation with ultraviolet light to the 5,6-cis-3-acetate (12) and the conversion of the material, to the desired 24,24-difluoro-1α,25-dihydroxyvitamin D₃ analog then is accomplished by saponification in mild base as already described.

BIOLOGICAL ACTIVITY

The biological potency of the new analog is confirmed by appropriate in vivo assays in the rat.

Male weanling rats are fed the low-calcium vitamin D-supplemented diet of Suda et al (J. Nutr. 100, 1049-1052 (1970)) for 3.5 weeks. They are then divided into 3 groups of 5-6 animals each. The animals of one group (the control group) receive 0.05 ml of ethanol by intrajugular injection. The second and third groups receive a known amount of 24,24-difluoro-1α,25-dihydroxyvitamin D₃ (24,24—F₂—1,25—(OH)₂D₃) and 1α,25-dihydroxyvitamin D₃ (1α,25—(OH)₂D₃), respectively, as solutions in 0.05 ml ethanol by intrajugular injection. At the appropriate times, the effect of the test compounds on intestinal calcium transport and on serum calcium levels (a measure of bone calcium mobilization) are determined by standard assay procedures (Martin and DeLuca, Am. J. Phys. 216, 1351-1359 (1969), and Tanaka et al, Biochemistry 14, 3293-3296 (1975)) with the following results:

| Biological Activity of 24,24-F₂-1,25-(OH)₂D₃ | | | |
|---|---|---|---|
| Compound Given | Dose (pmole) | Hours After Dose | Intestinal Ca Transport ($^{45}$Ca seros/ $^{45}$Ca mucos) | Serum Calcium mg/ 100 ml |
| EtOH | | | 1.9 ± 0.4$^a$ | 3.2 ± 0.1$^a$ |
| 24,24-F₂-1,25-(OH)₂D₃ | 65 | 6 h | 4.6 ± 0.8$^b$ | 4.3 ± 0.2$^b$ |
| | | 24 h | 4.7 ± 0.9$^c$ | 4.1 ± 0.3$^b$ |
| 1,25-(OH)₂D₃ | 65 | 6 h | 4.8 ± 0.7$^d$ | 4.2 ± 0.3$^b$ |
| | | 24 h | 5.7 ± 0.7$^e$ | 4.1 ± 0.4$^c$ |
| Significance of difference | | | b,c,d,e from a | b from a |

| Biological Activity of 24,24-F₂-1,25-(OH)₂D₃ | |
|---|---|
| $P < 0.001$; | $P < 0.001$; |
| c from e | c from a |
| not significant; | $P < 0.005$; |

These foregoing data indicate that 24,24-F₂-1,25-(OH)₂D₃, is active both in intestine and in bone, and that the compound is at least as potent as 1,25-(OH)₂D₃, the most active of the vitamin D derivatives heretofore known.

The 24,24-difluoro-1α,25-dihydroxycholecalciferol and 24,24-difluoro-1α,25-dihydroxy-5,6-trans-cholecalciferol compounds of this invention may be readily administered as sterile parenteral solutions by injection or intravenously or by alimentary canal in the form of oral dosages, or by suppository. Doses of from about 0.1 μg to about 2.5 μg per day are effective in obtaining the physiological calcium balance responses described and which are characteristic of vitamin D-like activity, with maintenance doses of about 0.25 μg being suitable.

Dosage form of the compounds can be prepared by combining them with a non-toxic pharmaceutically acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated, the end results being sought in a particular case, as well as other factors known to those skilled in the art in the therapeutic use of such medicinal agents.

We claim:
1. 24,24-difluoro-1α,25-dihydroxycholecalciferol.
2. The compound of claim 1 in crystalline form.
3. 24,24-difluoro-1α,25-dihydroxy-5,6-trans-cholecalciferol.
4. The compound of claim 3 in crystalline form.

* * * * *